(12) United States Patent  
Lee

(10) Patent No.: US 8,771,359 B2
(45) Date of Patent: Jul. 8, 2014

(54) SPINAL IMPLANT DEVICE

(76) Inventor: Daniel Dongwahn Lee, Las Vegas, NV (US)

( * ) Notice: Subject to any disclaimer, the term of this patent is extended or adjusted under 35 U.S.C. 154(b) by 194 days.

(21) Appl. No.: 12/957,451

(22) Filed: Dec. 1, 2010

(65) Prior Publication Data

US 2012/0143335 A1    Jun. 7, 2012

(51) Int. Cl.
*A61F 2/44* (2006.01)
(52) U.S. Cl.
CPC ................................. *A61F 2/4455* (2013.01)
USPC ....................................................... 623/17.16
(58) Field of Classification Search
USPC ........................ 623/17.11, 17.12, 17.15, 17.16
See application file for complete search history.

(56) References Cited

U.S. PATENT DOCUMENTS

| | | | |
|---|---|---|---|
| 4,554,914 A * | 11/1985 | Kapp et al. | 606/86 A |
| 5,336,223 A | 8/1994 | Rogers | |
| 5,620,444 A | 4/1997 | Assaker | |
| 7,674,296 B2 * | 3/2010 | Rhoda et al. | 623/17.15 |
| 8,123,808 B2 * | 2/2012 | Dewey et al. | 623/17.12 |
| 2003/0083659 A1 | 5/2003 | Lin et al. | |
| 2006/0217712 A1 | 9/2006 | Mueller et al. | |
| 2007/0191846 A1 | 8/2007 | Bruneau et al. | |
| 2007/0288011 A1 | 12/2007 | Logan | |
| 2008/0039948 A1 | 2/2008 | Biedermann et al. | |
| 2008/0058931 A1 * | 3/2008 | White et al. | 623/17.11 |
| 2008/0167720 A1 | 7/2008 | Melkent | |
| 2008/0167726 A1 * | 7/2008 | Melkent | 623/23.48 |
| 2009/0138083 A1 | 5/2009 | Biyani | |
| 2009/0138089 A1 | 5/2009 | Doubler et al. | |
| 2009/0164018 A1 * | 6/2009 | Sommerich et al. | 623/17.16 |
| 2010/0016971 A1 | 1/2010 | Berry | |
| 2010/0063510 A1 * | 3/2010 | Arlet et al. | 606/93 |
| 2010/0087924 A1 * | 4/2010 | Arlet | 623/17.12 |
| 2010/0249934 A1 * | 9/2010 | Melkent | 623/17.16 |
| 2010/0268343 A1 | 10/2010 | Dewey et al. | |
| 2010/0274288 A1 | 10/2010 | Prevost et al. | |

OTHER PUBLICATIONS

Intern'l Search Report/Written Opinion of the International Searching Authority, Appln. No. PCT/US2011/062597, Filing Date: Nov. 30, 2011, Mailing Date: Mar. 21, 2012, 11 pgs.

* cited by examiner

*Primary Examiner* — Ellen C Hammond
(74) *Attorney, Agent, or Firm* — Katten Muchin Rosenman LLP

(57) ABSTRACT

The present specification contemplates a spinal implant device that goes into, for example, a corpectomy defect in any part of the spine. In one aspect, the device is substantially tubular and is comprised of two hollow rods that coaxially slide on one another. The device can thus then expand in length and can be locked or fixed at a particular length. The device is hollow to configure a malleable trocar to be placed into the device. With this trocar, polymethymethacrylate (PMMA) can be injected and packed into the vertebral body cephlad and caudad. Finally the device can be locked at a desired length by crimping it or locking it using other fastening means.

15 Claims, 22 Drawing Sheets

50 (injection position)

50 (injection position)

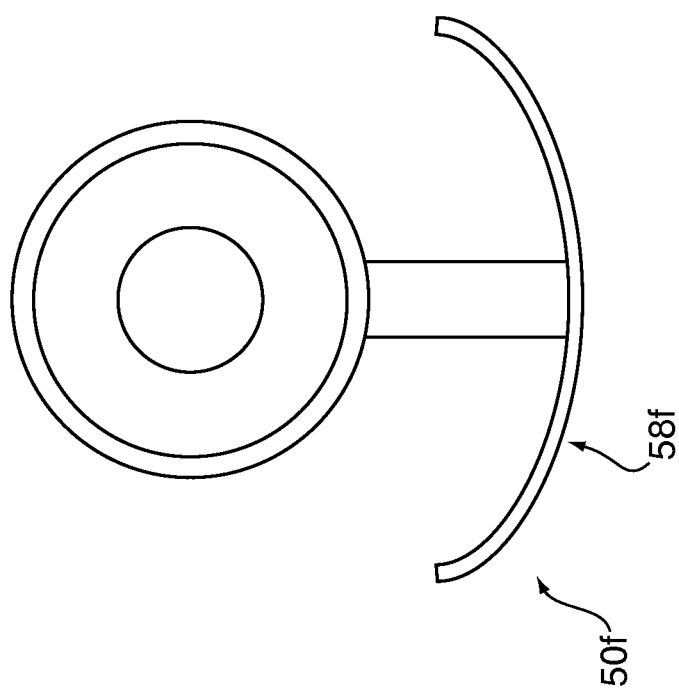

US 8,771,359 B2

SPINAL IMPLANT DEVICE

FIELD

The present specification relates generally to medical devices and more particularly relate to a spinal implant device.

BACKGROUND

A healthy spine is important to quality of life. In addition to muscular-skeletal support, it is also the central pathway for the nervous system. Many spinal defects can occur which may be mitigated or even repaired through spinal surgery. Corpectomy is one particular type of spinal surgery that typically involves removal of a portion of a vertebral body and/or adjacent intervertebral discs. Such removal is often followed by a reconstruction procedure to provide the mechanical support that is lost by the removal.

SUMMARY

This present specification contemplates a spinal implant device that goes into, for example, a corpectomy defect in any part of the spine. In one aspect, the device is substantially tubular and is comprised of two hollow rods that coaxially slide on one another. The device can thus then expand in length and can be locked or fixed at a particular length. The device is hollow to configure a malleable trocar to be placed into the device. With this trocar, polymethymethacrylate (PMMA) can be injected and packed into the vertebral body cephlad and caudad. Finally this device can be locked at a desired length by crimping it or locking it using other fastening means.

Once inserted, additional PMMA can be packed around the device to allow for further stabilization. This result is roughly analogous to the use of rebar as a structural support of cement. The device can be further designed to have threads on both sides of the implant so as to screw into the body above or below. It can be cannulated or noncannulated/solid.

The device can be configured in various dimensions and diameters for the appropriate purpose. The device may be particularly suitable for sites that are not amenable to traditional implants.

The device is contemplated for use in, as a non-limiting example, any corpectomy defect. The device can be sized differently for large or small spines. The device may also be used for spines with osteoporotic bone or difficult to access places. The device may be used for patients with cancer who need instant stabilization.

BRIEF DESCRIPTION OF THE DRAWINGS

FIG. 22 shows an end view of the drip tray of FIG. 20.

DETAILED DESCRIPTION

Figure 1:
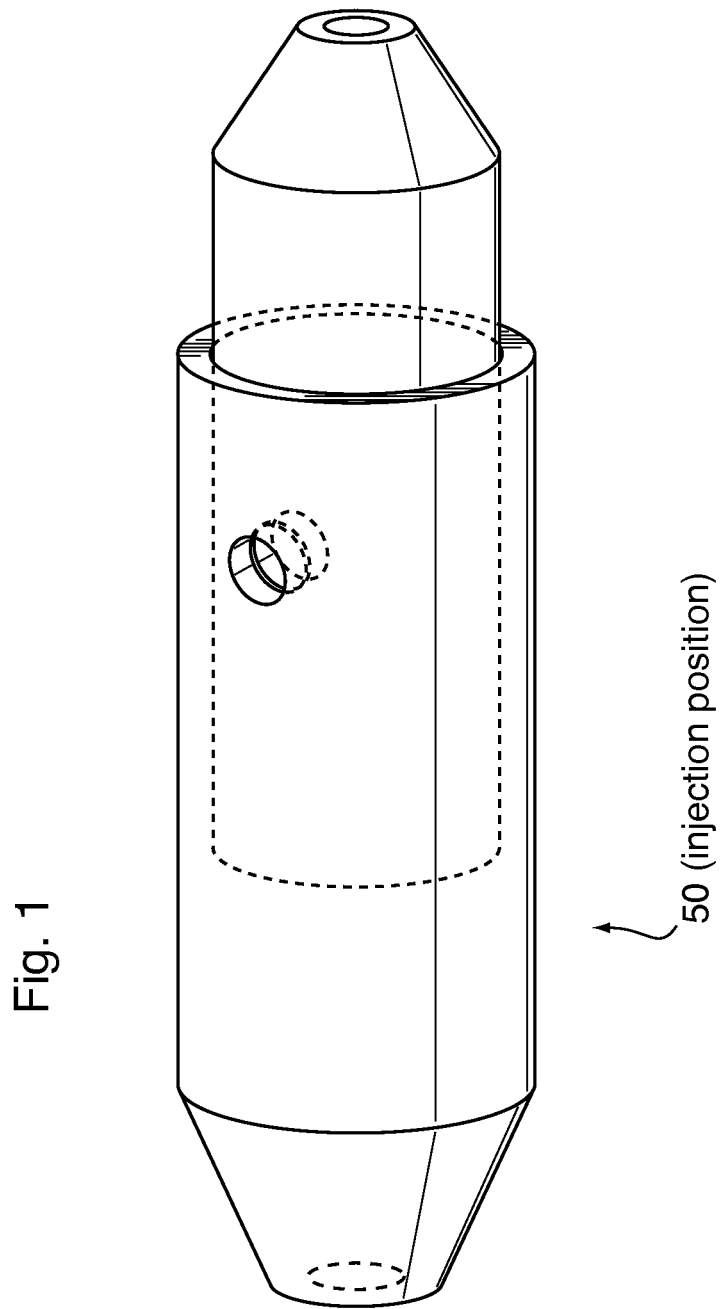
FIG. 1 shows a side-sectional view of a spinal implant device.
Figure 2:
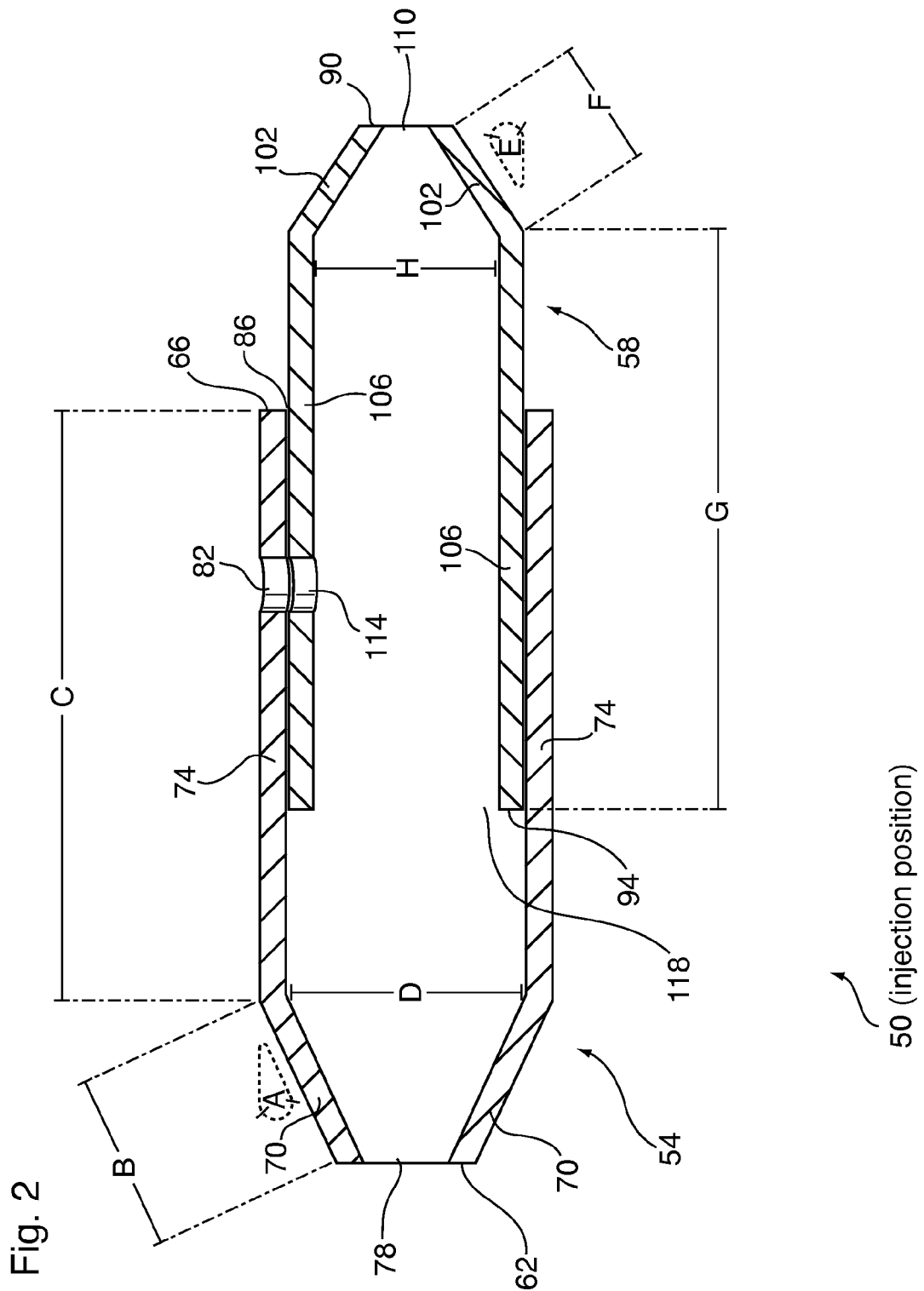
FIG. 2 shows the spinal implant device of FIG. 1 with character reference labels.

Referring now to FIG. 1 and FIG. 2, a spinal implant device is indicated generally at 50. Device 50 can be made from any suitable non-toxic or bio-compatible material, such as medical-implant grade stainless steel or plastic. Other materials can include titanium, polyetherketone (PEEK), polyetherketone (PEK), polyetherketoneketone (PEKK), polyetherimide, or polyphenylsulfone, and bismuth trioxide ($BiO_3$) or other material with radioopacity such that it can be viewed under an imaging beam with reduced or minimal artifacts.

For illustrative convenience, FIG. 1 shows device 50 without specific character reference labels, while FIG. 2 includes such labels. Referring now to FIG. 2, device 50 comprises a first hollow rod 54 that is configured to slidably receive a second hollow rod 58 therein.

First hollow rod 54 comprises a distal end 62 and a proximal end 66. A tapered section 70 and a cylindrical section 74 interconnects distal end 62 and proximal end 66.

Distal end 62 comprises an opening 78 that communicates the interior of device 50 with the exterior of device 50.

Tapered section 70 comprises an angle A and a length B that is configured so that tapered section 70 can be driven into a vertebral body.

Cylindrical section 74 comprises a length C that is about half the distance of a reconstruction space left by a corpectomy. Further understanding about the selection of length C will become apparent from the following discussion. Cylindrical section 74 has a substantially uniform inside diameter D along its length ending at the wider end of tapered section 70.

Diameter of opening 78 can be selected to be forty percent of diameter D, and likewise the diameter of opening 110 can be selected to be forty percent of diameter H. The taper, as defined by B and A, and by F and E. Can be selected so that B is about .5 cm and F is about .5 cm. The angles A and E can be selected to substantially correspond to the taper of the trocar chosen to make a pilot hole in the target vertebral body.

Cylindrical section 74 also comprises a port 82 which provides communication from the exterior of device 50 to the interior of device 50. As will be discussed further below, port 82 is configured to receive a malleable trocar so that a bone cement, such as polymethylmethacrylate (PMMA) can be injected into port 82 and be expressed from opening 78. Port 82 typically has a circular opening that defines a cylindrical passage towards the interior of device 50.

Proximal end 66 defines its own opening 86. Opening 86 has a diameter that substantially corresponds to inside diameter D and is configured to receive second hollow rod 58 therein, so that second hollow rod 58 can slidably move within cylindrical section 74.

The wall thickness of first hollow rod 54 is selected, with due consideration to the material used to construct hollow rod 54, to provide be sufficiently rigid to pierce veterbral bone and to also to provide at least a certain degree of mechanical support as part of a reconstruction following a corpectomy.

Second hollow rod 58 is structurally quite similar to first hollow rod 54 and when device 50 is assembled as shown in FIG. 2, second hollow rod 58 is almost a mirror image of first hollow rod 54 except differently dimensioned so that second hollow rod 58 can be slidably received within first hollow rod 54.

Accordingly, second hollow rod 58 also comprises a distal end 90 and a proximal end 94. Likewise, a tapered section 102 and a cylindrical section 106 interconnects distal end 90 and proximal end 94.

Distal end 90 comprises an opening 110 that communicates the interior of device 50 with the exterior of device 50. As discussed above, PMMA injected via port 82 may be expressed from opening 110.

Tapered section 102 comprises an angle E and a length F that is configured so that tapered section 102 can be driven into a vertebral body. Angle E and length F may be different from angle A and angle B due to the overall smaller size of second hollow rod 58, and yet are still selected for driving into a verterbral body.

Cylindrical section 106 comprises a length G that is about half the distance of a reconstruction space left by a corpectomy. However, length G may be longer than length C to accommodate the fact that a portion of cylindrical section 98 remains within cylindrical section 74 when device 50 is in an extended position, again discussed further below. Cylindrical section 106 has a substantially uniform inside diameter H along its length ending at the wider end of tapered section 102. The outer diameter of cylindrical section 106, not labeled, is slightly smaller than inside diameter D, such that leakage of injected PMMA from opening 86 is minimal or obviated, but still accommodating coaxial slidable movement of cylindrical section 106 within cylindrical section 74.

Various versions of device 50 can be provided having a different dimensions for one or more of A, B, C, D, E, F, G, or H, with each version being configured to accommodate the spines of persons of differing heights, weights, etc. The choice of angles can be influenced by the choice of a trocar or other instrument used to make a starter-hole in the corresponding vertebral body. Dimensions can also be chosen so that device 50 fit a vertebral balloon or kytoplasty balloon. As a non-limiting example, the tapers could be three times the diameter of the hole from which the cement is expressed; so that the taper is almost conical.

Cylindrical section 106 also comprises a port 114 that is alignable with port 82 to provide communication from the exterior of device 50 to the interior of device 50, and more specifically directly to the interior of cylindrical section 106. As will be discussed further below, port 114 is configured to receive a malleable trocar so that a bone cement, such as polymethylmethacrylate (PMMA) can be injected into port 82 and port 114 and be expressed from opening 110. Port 114 typically has a circular opening that defines a cylindrical passage towards the interior of cylindrical section 106 that has substantially the same dimensions as port 82.

Proximal end 94 defines its own opening 118. Opening 86 has a diameter that substantially corresponds to inside diameter D and is configured to receive second hollow rod 58 therein, so that second hollow rod 58 can slidably move within cylindrical section 74.

The wall thickness of second hollow rod 106 is selected, again with due consideration to the material used to construct hollow rod 106, to be sufficiently rigid to pierce vertebral bone and to also to provide at least a certain degree of mechanical support as part of a reconstruction following a corpectomy.

Figure 3:
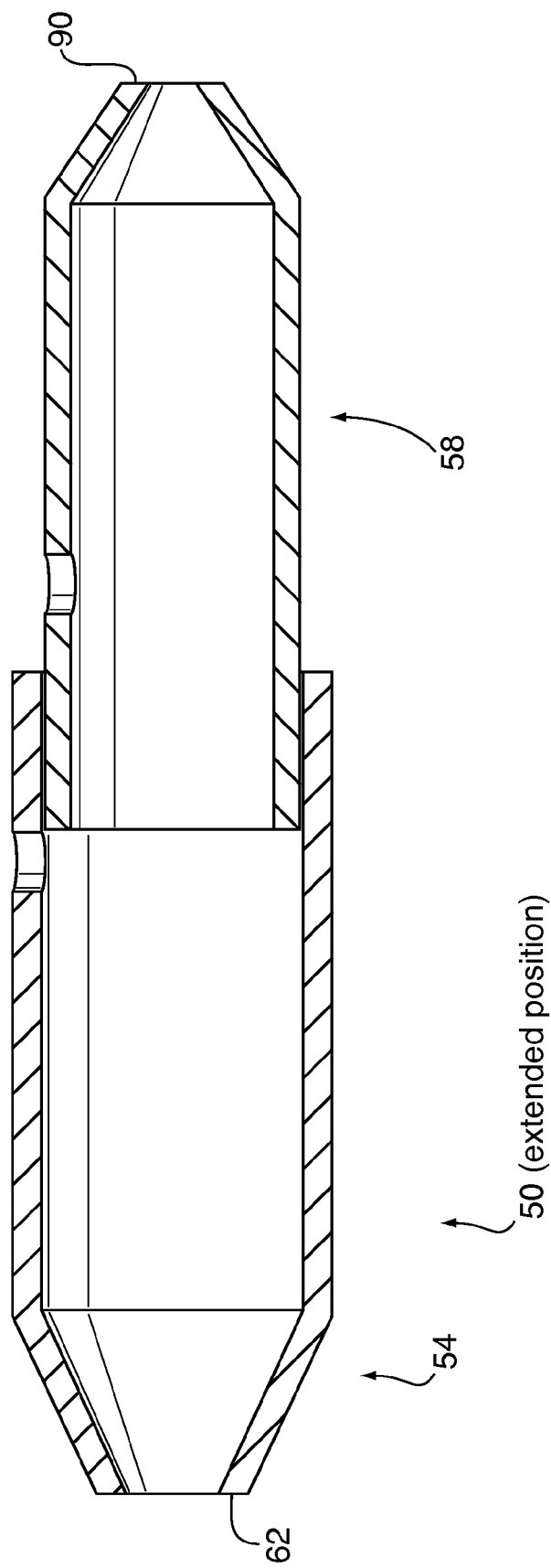
FIG. 3 shows the spinal implant device of FIG. 1 and FIG. 2 in an extended position, in contrast to the injection position shown in FIG. 1 and FIG. 2.

At this point it may be noted that FIG. 1 and FIG. 2 show device 50 in an injection position, whereby a substantial portion of cylindrical section 106 is coaxially encased by cylindrical section 74, and port 82 and port 114 are aligned. FIG. 3, in contrast to FIG. 1 and FIG. 2, shows device 50 in an extended position, whereby second hollow rod 58 has been slid outwardly from first hollow rod 54 such that the distance between distal end 90 and distal end 62 is farther apart in FIG. 3 than in FIG. 1 and FIG. 2.

Figure 4:
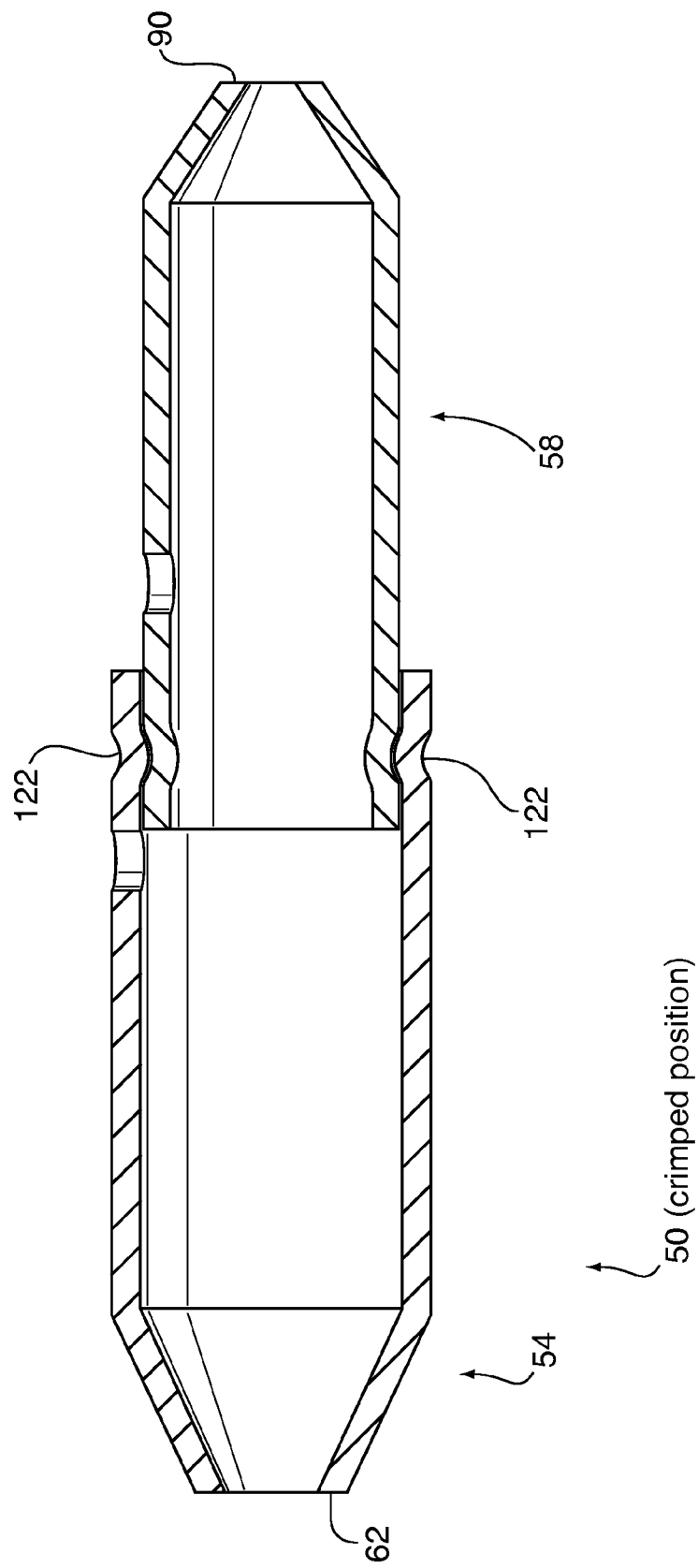
FIG. 4 shows the spinal implant device of FIG. 3 having a crimp applied to its diameter to keep each hollow rod fixed in relation to each other.

FIG. 4 also shows device 50 in the extended position of FIG. 3, but wherein a crimp 122 has been applied to the overlapping portions of first hollow rod 54 and second hollow rod 58 and thereby mechanically secure device 50 into the extended position. Note that a crimp 122 is but one means contemplated of mechanically securing device 50 into the extended position, and other means are contemplated. For example mechanical fastener could also be applied, such as an adhesive or a rivet or a screw.

Figure 5:
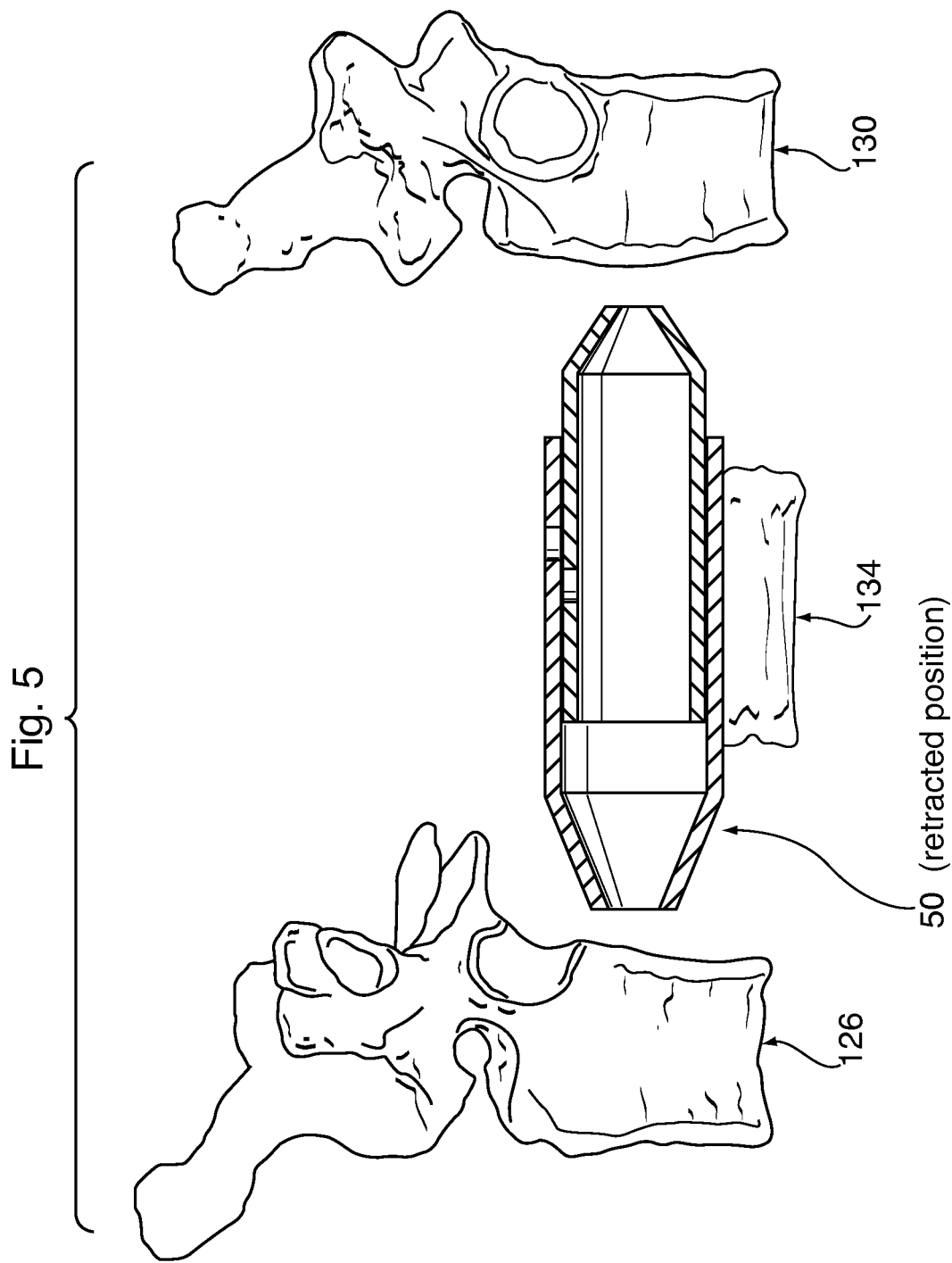
FIG. 5 shows the spinal implant device of FIG. 1 in situ and ready for deployment.

As will now be explained, device 50 can be used to strengthen or stabilize a portion of a vertebral column in various circumstances where the column may be weakened, such as for example as a result of a corpetomy. FIG. 5 shows device 50 in a fully retracted position whereby port 82 and port 114 are not aligned and cylindrical section 106 is encased by cylindrical section 74 distal end 90 and distal end 62 are closer together than in FIG. 1 and FIG. 2. In FIG. 5, device 50 is shown in situ between a first vertebral body 126 and a second vertebral body 130 and nestled in relation to a resected vertebral body 134 that is between first vertebral body 126 and a second vertebral body 130. It is to be understood that FIG. 5 is not intended to be to scale but rather is schematic in nature for illustrative purposes. Furthermore the example representation of resected vertebral body 134 is not intended to literally represent a resected vertebral body 134 but is intended to provide a schematic representation for illustrative purposes. Again, the reason for the resection of resected vertebral body 134 is not particularly limited, but can, for example, be the result of a corpectomy.

The view in FIG. 5 contemplates that the patient has been prepped and draped and that device 50 has been fully retracted so that device 50 can be implanted between first vertebral body 126 and second vertebral body 130 according to the teachings herein.

Figure 6:
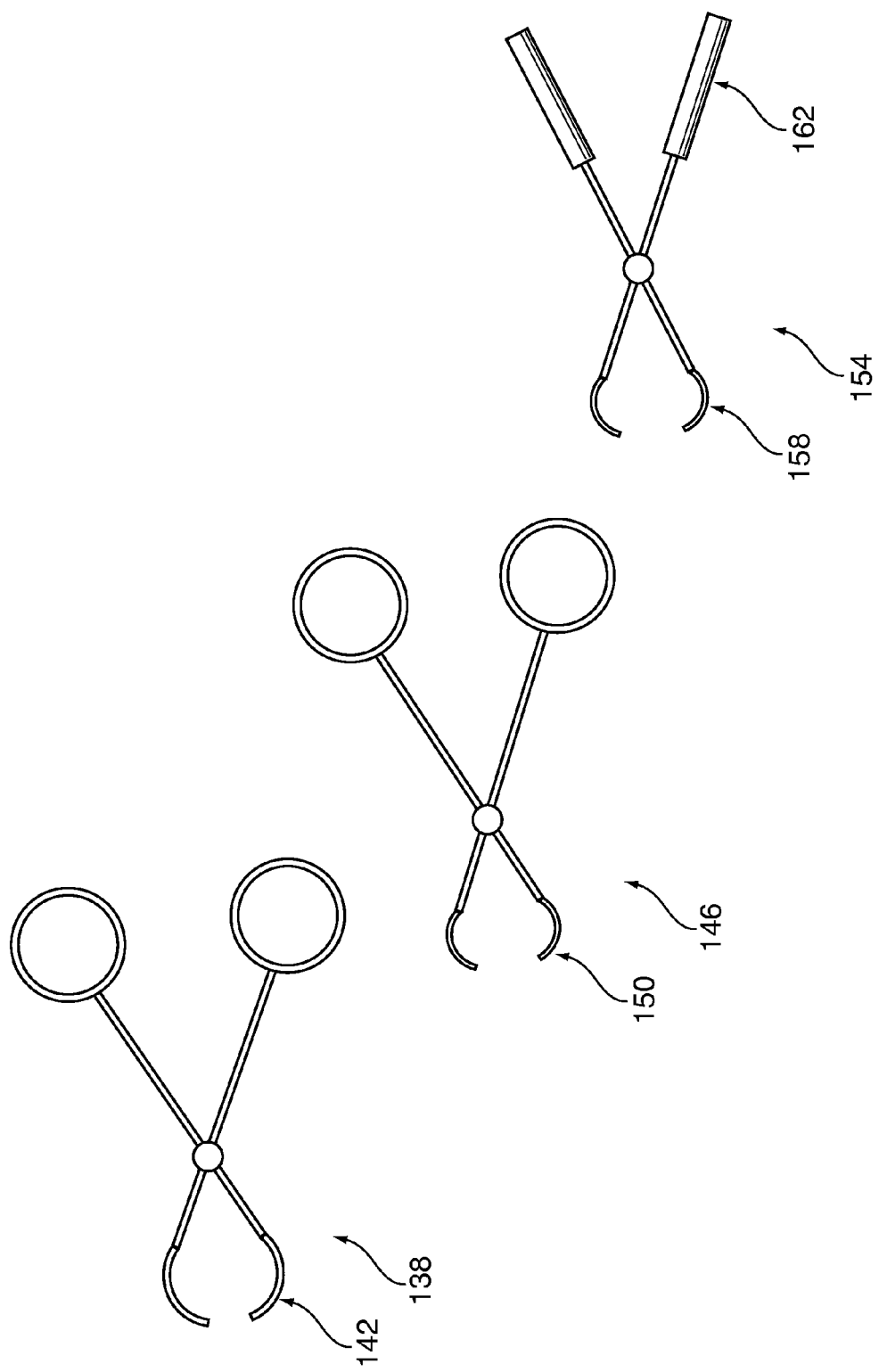
FIG. 6 shows a kit of example surgical tools instruments can be used to deploy the spinal implant device of FIG. 1.

FIG. 6 shows surgical instruments that are presently contemplated for use in completing the implantation of device 50 from the state shown in FIG. 5. A first clamp 138 is contemplated having a pair of jaws 142 with a complementary diameter to the exterior diameter of cylindrical section 74. Jaws 142 may have a rubber coating or other material that reduce slippage so that first hollow rod 54 can be held in a substantially fixed position, as discussed later below. A second clamp 146 is contemplated having a pair of jaw 150 complementary to the diameter of the exterior diameter of cylindrical section 106. Jaws 146 may have a rubber coating or other material that reduce slippage so that second hollow rod 58 can be moved coaxially in relation to first hollow rod 54 while first hollow rod 54 is held fixed using first clamp 138. While not shown, it is generally contemplated that clamp 138 and clamp 146 will each comprise a ratcheting locking mechanism, which permits jaws to progressively close but restricts jaws from opening unless a specific release is actuated on the ratcheting locking mechanism. Such ratcheting locking mechanisms are known in the art. A crimping tool 154 is also contemplated having a pair of jaws 158 that are formed so as to be able to form crimp 122 shown in FIG. 4. Crimping tool 154 also comprises a pair of handles 162 that can be squeezed in order to apply sufficient compressive force via jaws 158 to form crimp 122. Crimping tool 154 may also comprise a ratcheting locking mechanism. In a variation, not shown, each jaw 158 may comprise a boss or other protuberance to provide a dimpled crimp at the point where the boss contacts the rod, rather than forming a contiguous crimp around the entire diameter.

Figure 7:
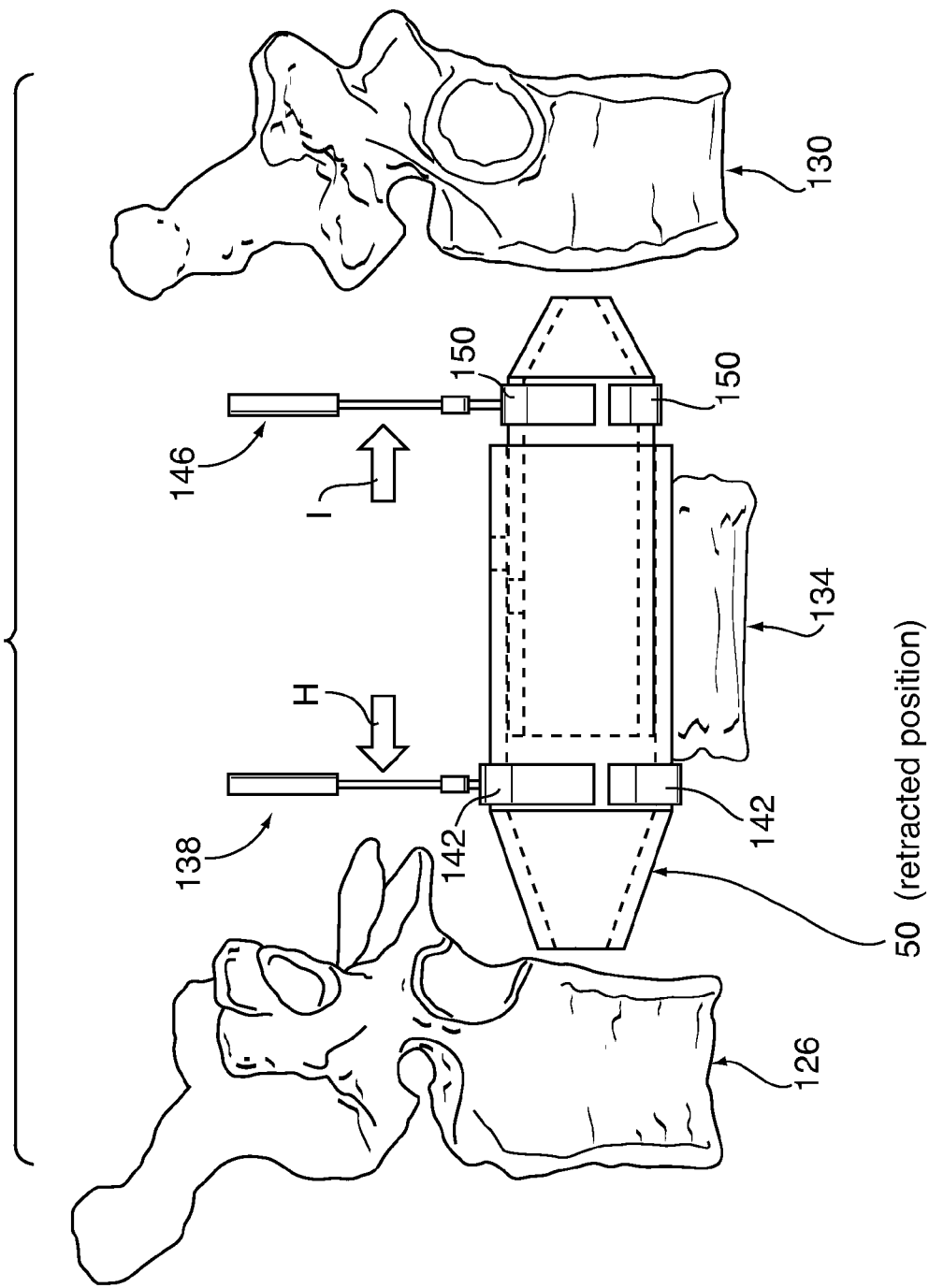
FIG. 7 shows the spinal implant device of FIG. 5 during deployment using the instruments from FIG. 6.

FIG. 7 shows the view of FIG. 5 except that jaws 142 of clamp 138 are shown as grasping first hollow rod 54, while jaws 150 of clamp 146 are shown grasping second hollow rod 58. In this event, first hollow rod 54 can be held fixed or moved along the direction of arrow H, second hollow rod 58 can also be held fixed or moved along the direction of arrow I. Using this technique, end 62 can be urged towards vertebral body 126, while end 90 is urged towards vertebral body 130. Likewise end 62 can be manipulated to pierce vertebral body 126 if desired and affix end 62 therein, while end 90 can be manipulated to pierce vertebral body 130 if desired and affix end 90 therein.

Figure 8:
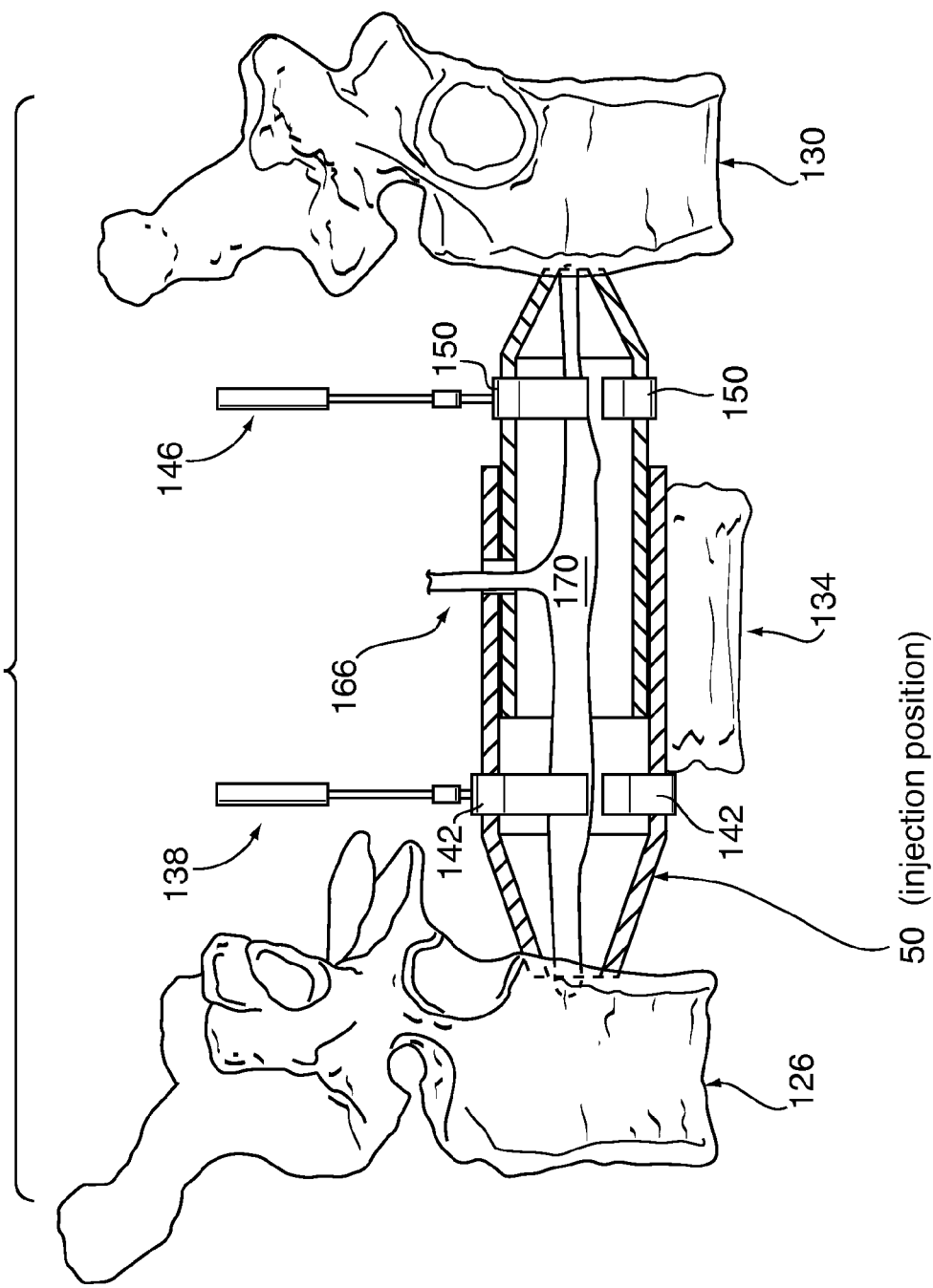
FIG. 8 shows the spinal implant device of FIG. 7 during injection of bone cement via the spinal implant device during deployment using the instruments from FIG. 6.

As a result of the actions described in relation to FIG. 7, device 50 is eventually adjusted into the injection position as shown in FIG. 8. Clamp 138 or clamp 146 may be now removed, or continued to be used to retain device 50 in the injection position. In FIG. 8 clamp 138 and claim 146 are still shown as being used to retain device 50. A flexible trocar 166 is also represented in FIG. 8, which is used to inject PMMA 170 or other curable flowable bone cement into device 50 and express PMMA 170 from opening 78 into the vicinity of vertebral body 126 and from opening 110 into the vicinity of vertebral body 130. While not shown in FIG. 8, it is contemplated that trocar 166 may be inserted toward either opening 78 or toward opening 110 to direct more PMMA 70 to the respective vertebral body 126 or vertebral body 130. Trocar 166 can thus be of different lengths so that PMMA 170 exits at a desired location. A syringe (not shown) or other injecting device may also be connected to trocar 166 to urge PMMA 170 into trocar 166.

Figure 9:
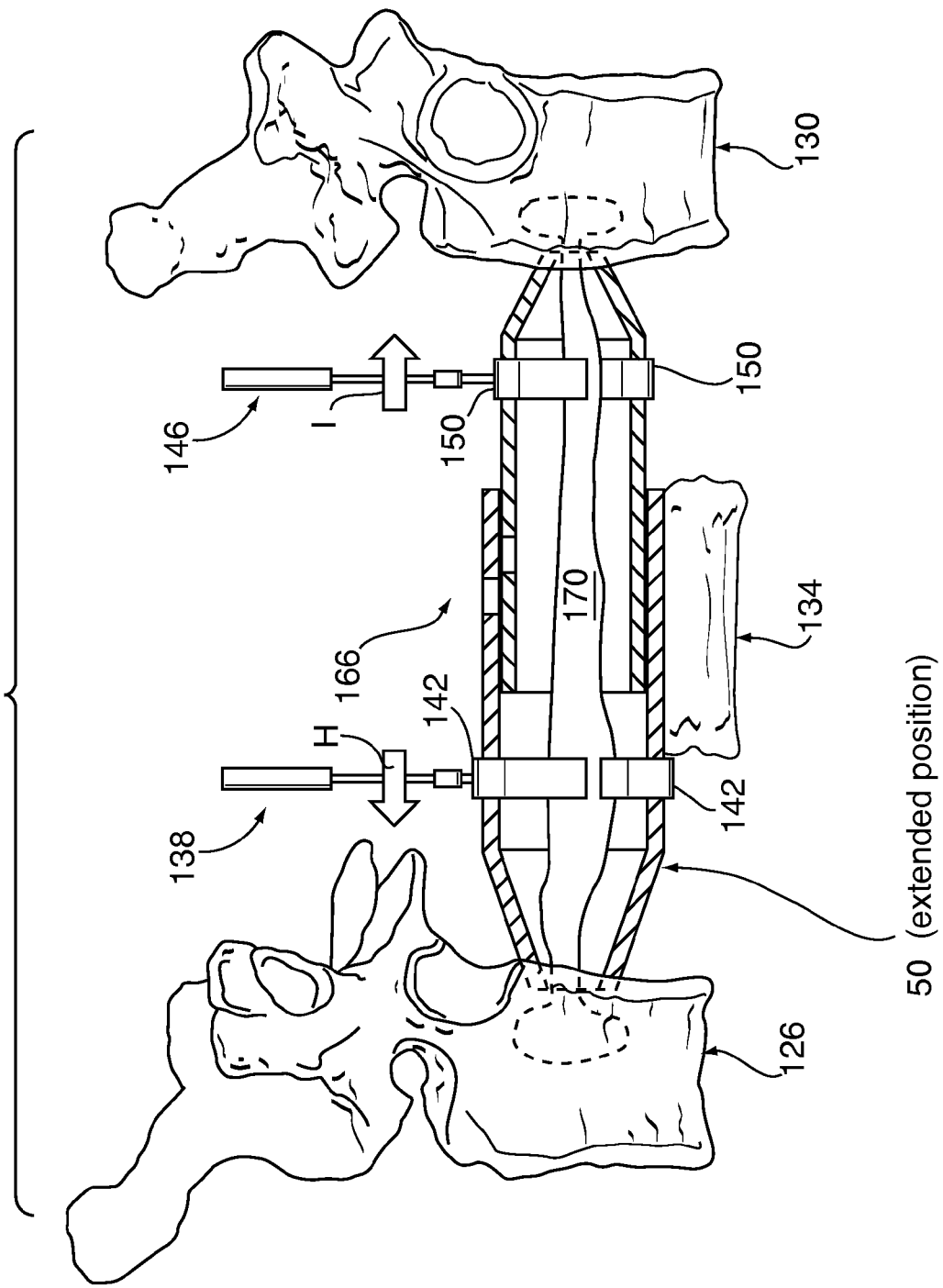
FIG. 9 shows the spinal implant device of FIG. 8 during further deployment of the device into surrounding vertebra using the instruments from FIG. 6.
Figure 10:
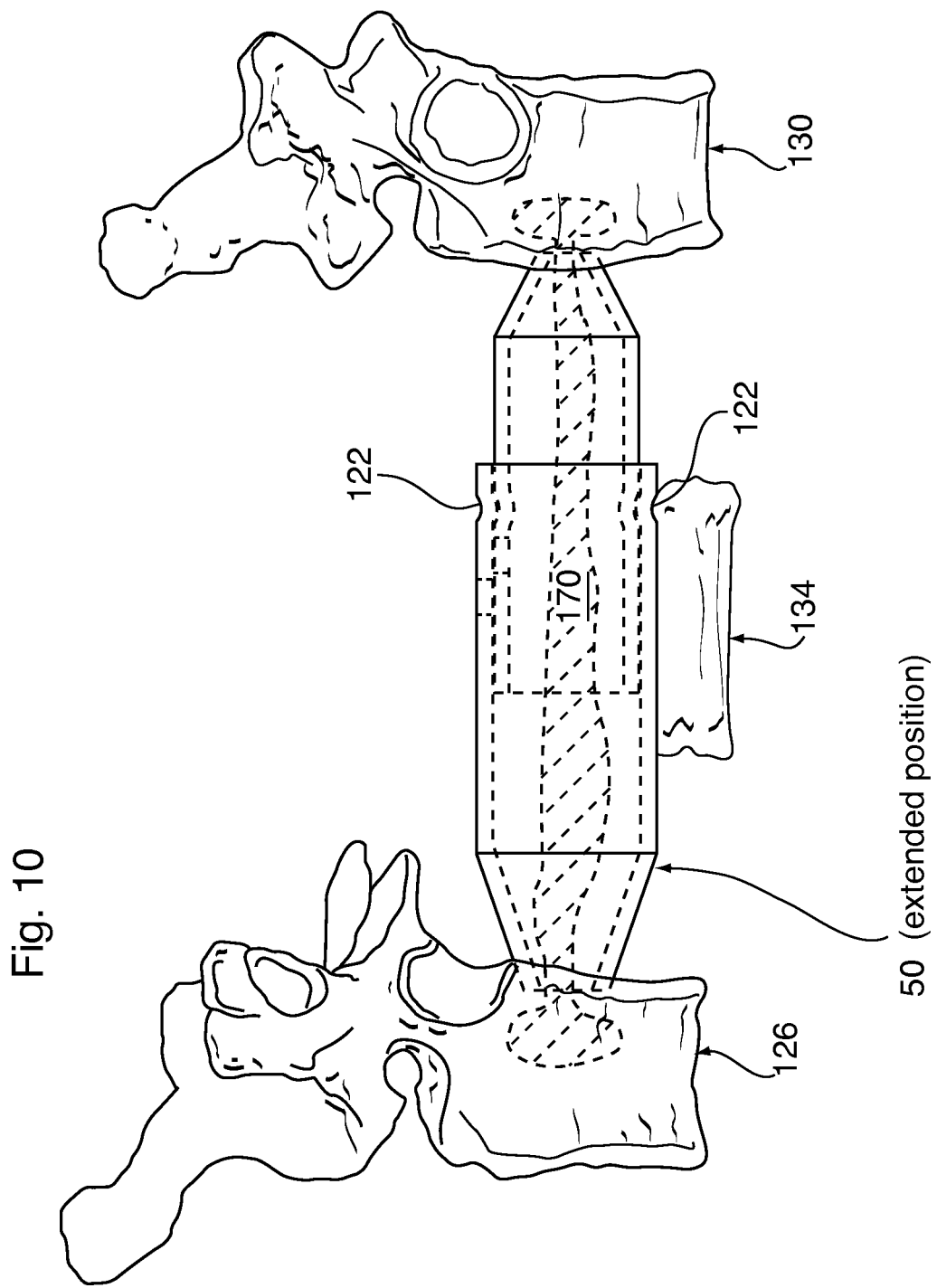
FIG. 10 shows the spinal implant device of FIG. 9 fully deployed.

Referring now to FIG. 9, it is contemplated that the injection of PMMA 170 is complete and that trocar 166 has been removed. Furthermore, FIG. 9 contemplates, if desired, the further movement of first hollow rod 54 along the direction of arrow H to further embed end 62 into vertebral body 126, or the further movement of second hollow rod 58 along the direction of arrow I to further embed end 90 into vertebral body 130.

A number of other embodiments are contemplated. For example, tapered section 70 or tapered section 102 or both of them could be provided with exterior threads, such that rotation of a respective rod will bite into a respective surrounding vertebral body. Such threading would further mechanically secure device 50.

Figure 11:
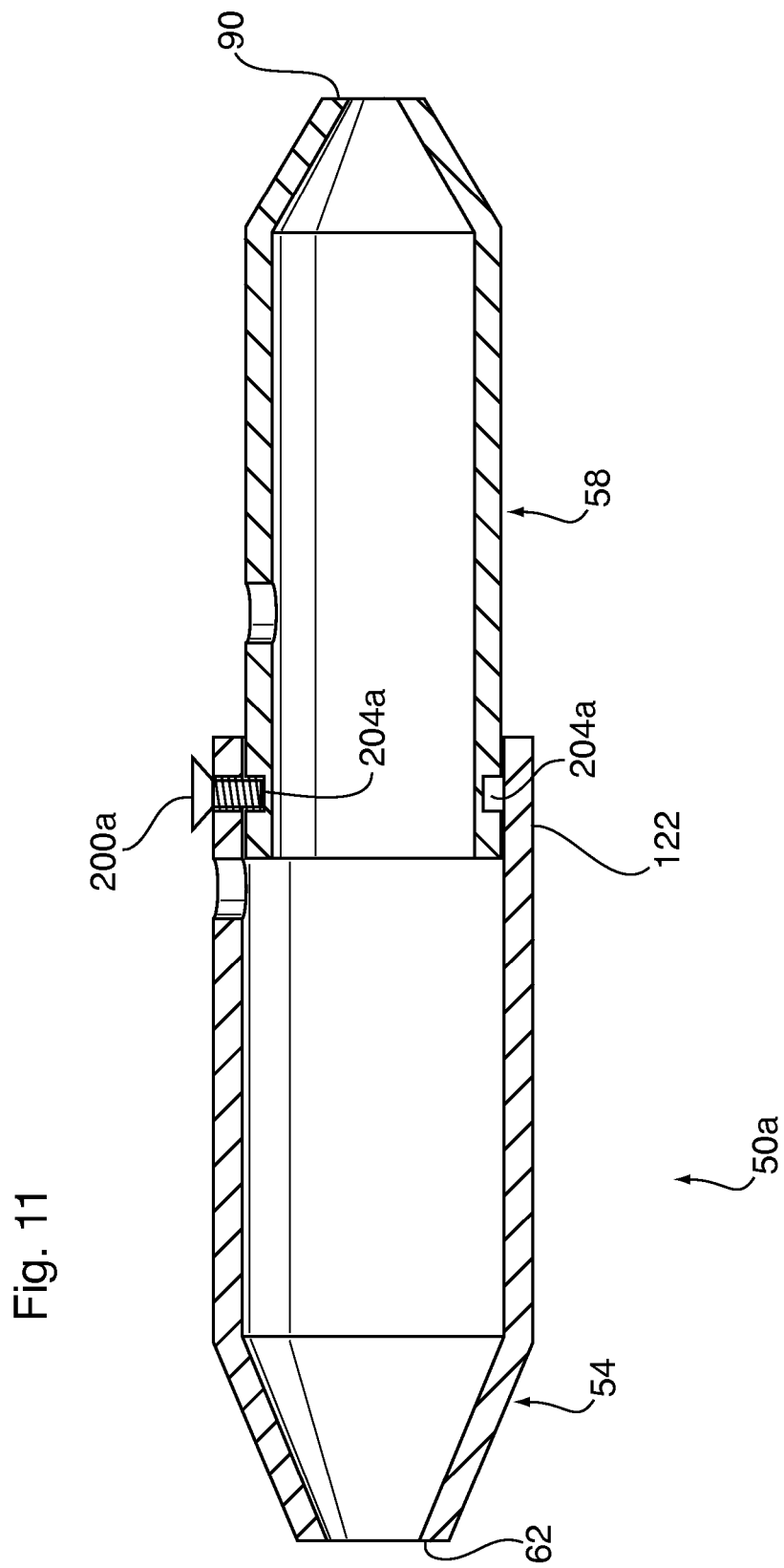
FIG. 11 shows an alternative embodiment utilizing a set screw rather than a crimp.

Another embodiment is shown in FIG. 11, wherein a modified version of device 50, shown as device 50a is provided. In device 50a, crimp 122 is obviated and in its place, a set screw 200a is provided for affixing rod 54 to rod 58. One or more channels 204a (or the like) may be provided about the periphery of rod 58 in order to receive set screw 200a, such that when set screw 200a is fully tightened its tip occupies channel 204a and thereby secures rod 54 to rod 58.

Figure 12:
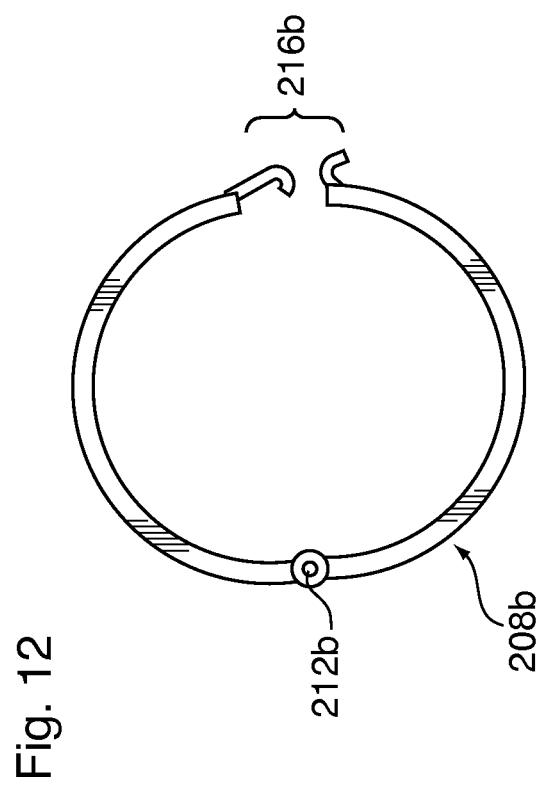
FIG. 12 shows an alternative embodiment utilizing a lock ring which can be used rather than a crimp.
Figure 13:
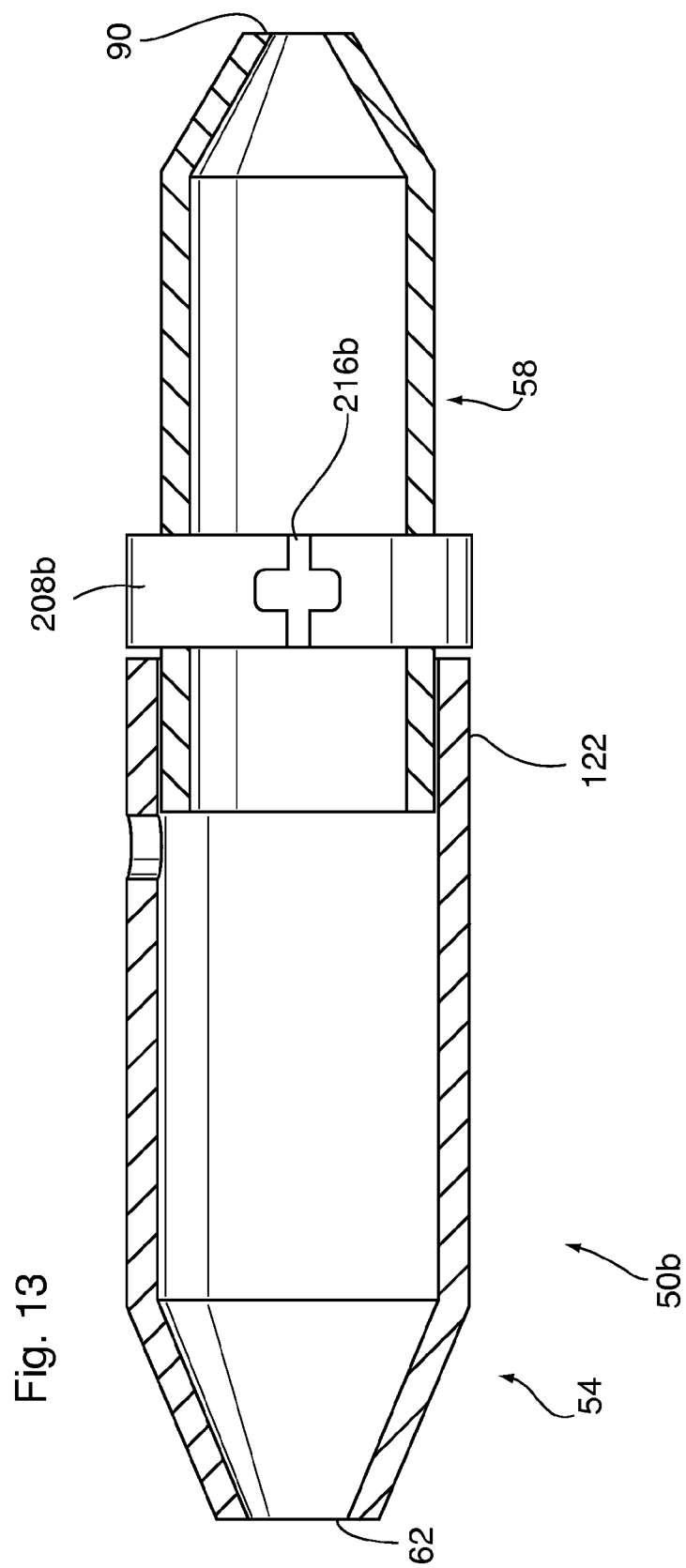
FIG. 13 shows the lock ring of FIG. 12 in use.

A further alternative to crimping is shown in FIG. 12 and FIG. 13. FIG. 12 shows a side-view of a lock ring 208b having a hinge 212b and a clasp 216b. Lock ring 208b can be unclasped, as shown in FIG. 12, and the halves opened so that lock ring 208b can be placed around rod 58. The diameter of lock ring 208b, and the clasp 216b are sized to be securely affixed to rod 58, so that rod 54 is prevented from sliding along the length of rod 58, as shown in FIG. 13.

Figure 14:
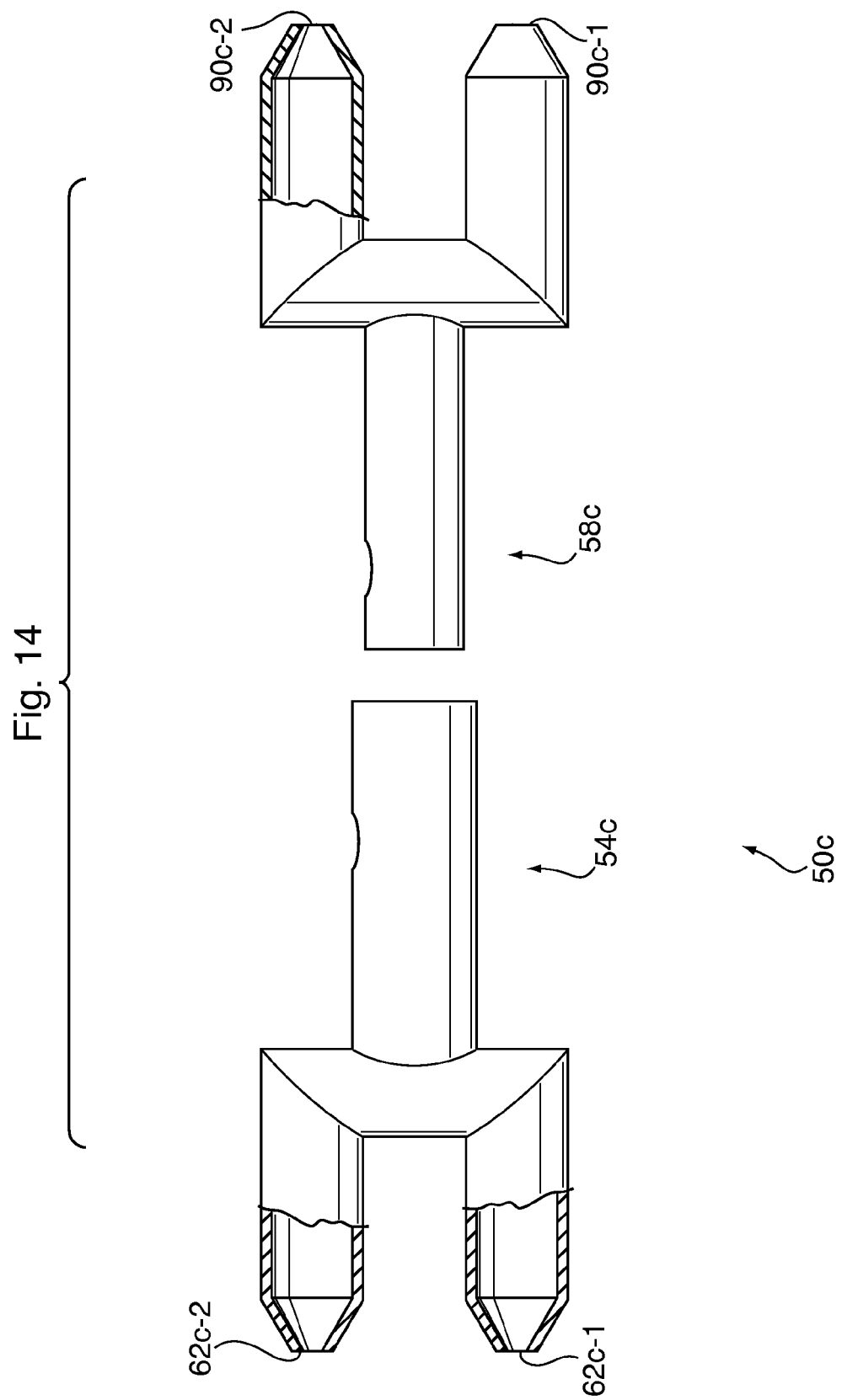
FIG. 14 shows an alternative embodiment with forked ends for each rod.

Another embodiment is shown in FIG. 14, wherein a modified version of first hollow rod 54c and second hollow rod 58c are provided. First hollow rod 54c and second hollow rod 58c each have a forked tip configuration. Bone cement can be expressed out of one or more of each end 62c-1 or end 62c-1 and out of one or more of each end 90c-1 or end 90c-2. Each fork may be driven into a respective vertebral body to secure its respective rod therein.

Figure 15:
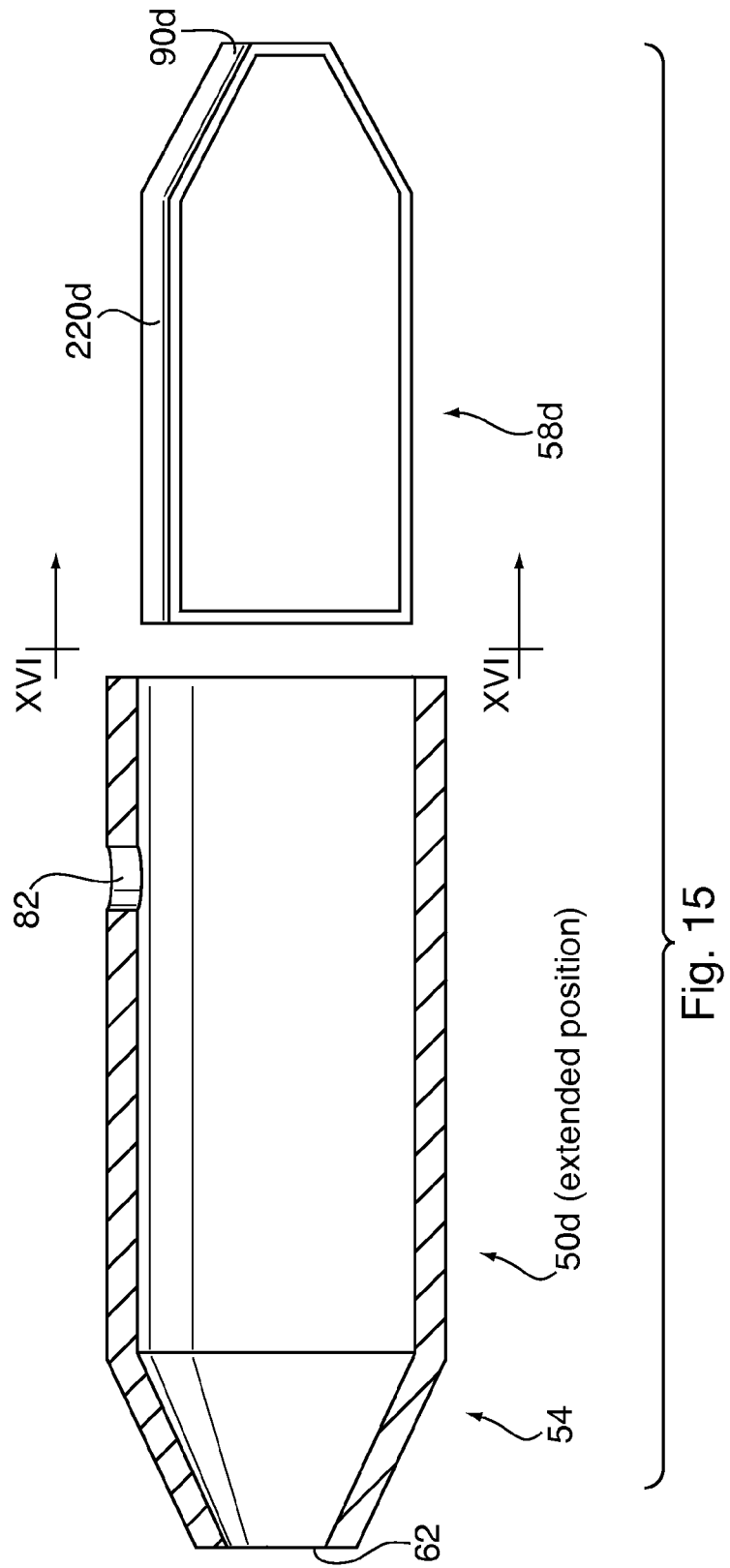
FIG. 15 shows an alternative embodiment wherein one of the rods is solid and has a channel for flowing bone cement therealong.
Figure 16:
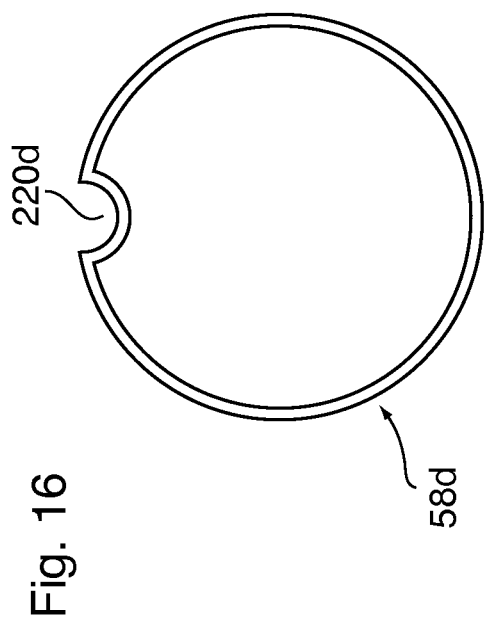
FIG. 16 is an end view of the solid rod of FIG. 15 through the lines XVI-XVI.

Another embodiment is shown in FIG. 15 and FIG. 16 and indicated as device 50d. In device 50d, first hollow rod 54 is the same as used in device 50. However, second rod 58d is substantially solid but comprises a channel 220d along its length. Channel 220d can be aligned with port 82 so that delivered bone cement travel therealong and exits from tip 90d.

A further variation on device 50d (not shown) contemplates the provision of one or more channels, (like channel 220d) along either the exterior or rod 58 and a corresponding boss along the interior of rod 54 that fits within the channel. In this manner, rod 54 and rod 58 can slide coaxially with each other, but cannot rotate in relation to each other. Other mechanical means to permit coaxial movement while restricting rotational movement will occur to those skilled in the art. Such channel and boss combinations can be about three millimeters, for example.

In another variation, port 82 can be a slot that run along a portion of the length of rod 54, rather than the hole as shown in FIG. 15.

Figure 17:
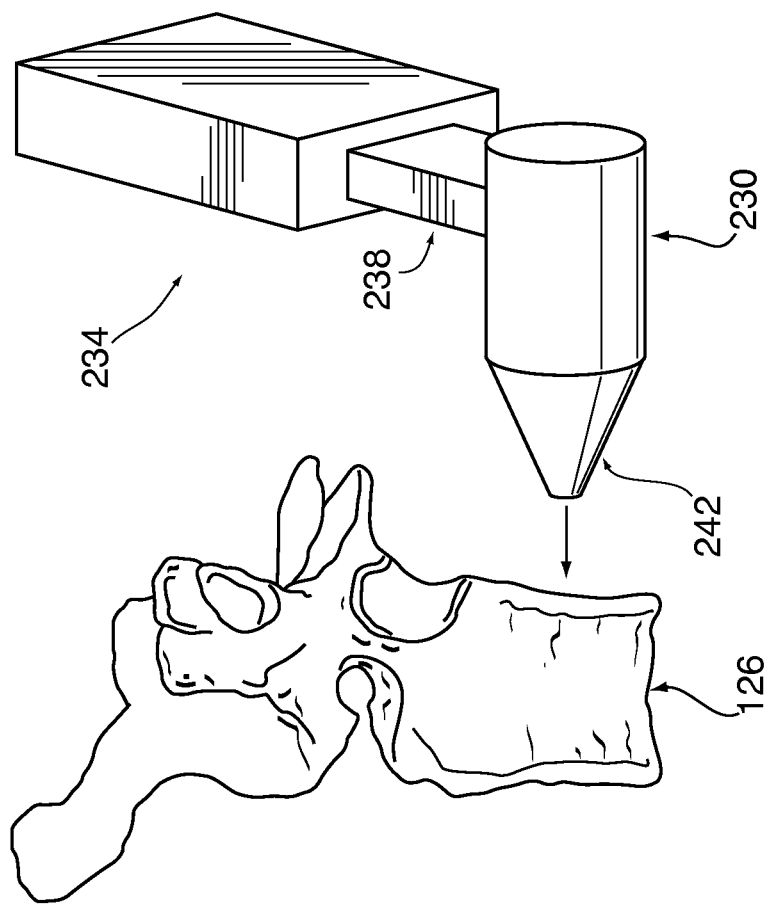
FIG. 17 shows another surgical instrument that can be used with the spinal implant devices.

Another embodiment is shown in FIG. 17 in the form of a solid trocar 230 having a handle 234, a shaft 238 and a tip 242. Tip 242 is oriented at a ninety degree angle in relation to handle 234. It is contemplated that before insertion of device 50 (or any of its variants), trocar 230 can be used to make a pilot hole in an appropriate vertebral body, such a hole being then used to receive a respective end of device 50 (or its variants).

Figure 18:
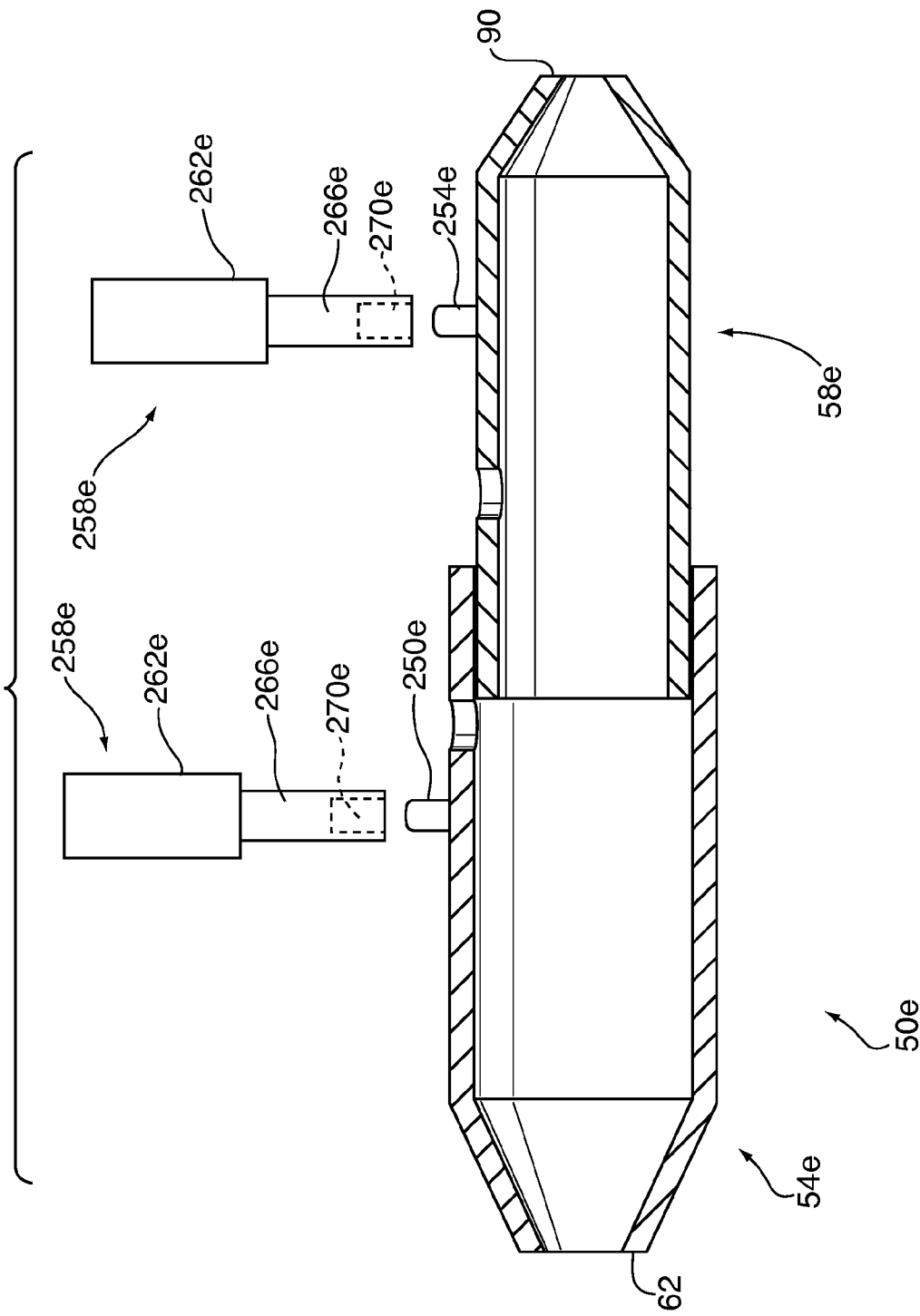
FIG. 18 shows an alternative embodiment for the spinal implant device of FIG. 1 and surgical instruments that can be used therewith.

Another embodiment is shown in FIG. 18 in the device 50e that is substantially the same as device 50 but also comprises a first boss 250e on first hollow rod 54e and a second boss 254e on second hollow rod 58e. Additionally a pair of surgical instruments 258e are provided having a handle 262e and a shaft 266e with a chamber 270e for receiving boss 250e and boss 254e respectively. Device 50e can be used in combination with instruments 258e as an alternative to the use of clamp 138 and clamp 146 in association with device 50.

In some implementations, it is contemplated that bone cement or PMMA will overflow and surround the exterior of device 50, and not simply be confied to the interior of device 50 or the adjacent vertebral bodies. In this situation, bosses 250e and 254e can also additionally provide reinforcement as PMMA cures around each boss 250e, 254e. It can thus be desired to provide a plurality of bosses on each rod to provide such reinforcement once PMMA cures.

Figure 19:
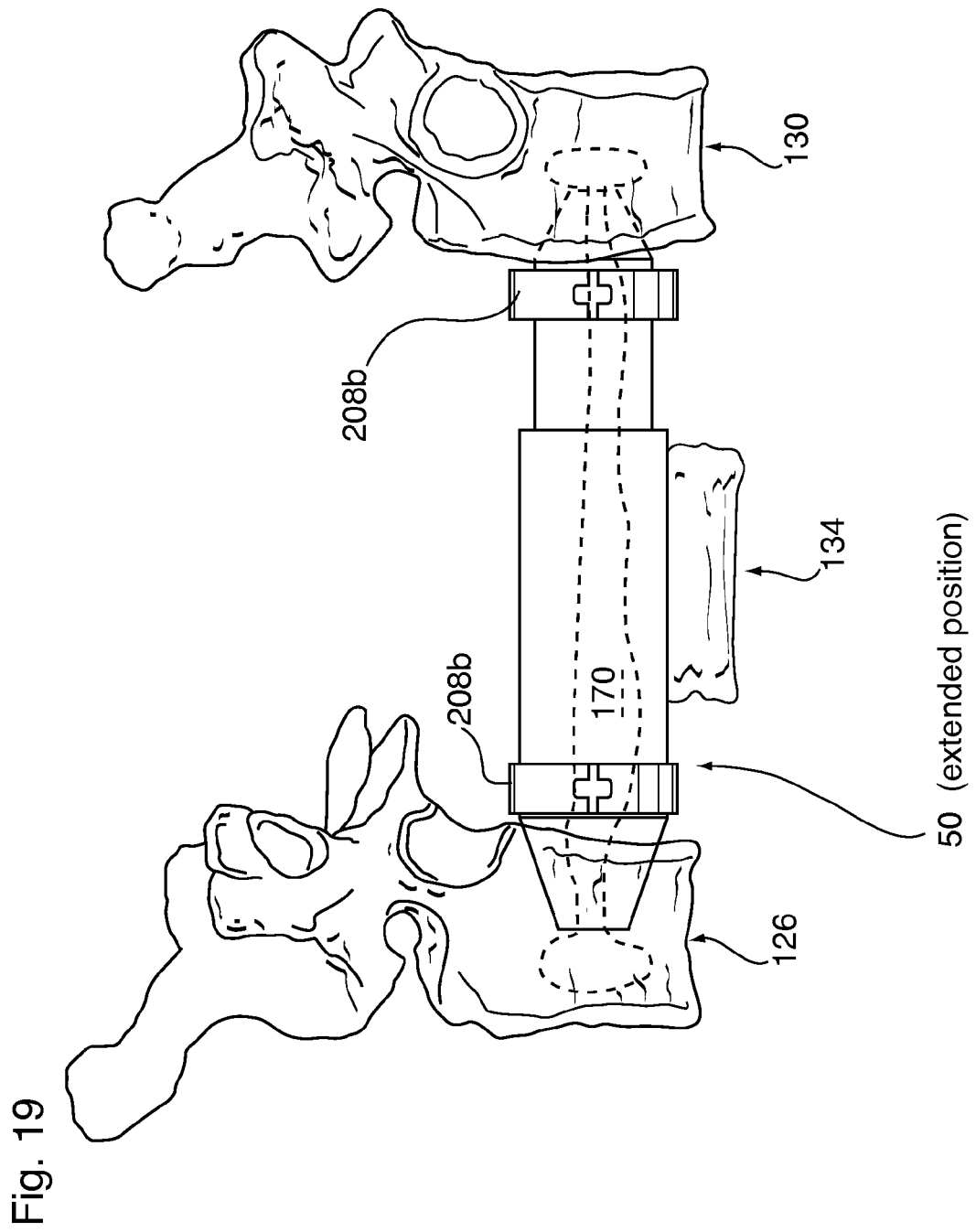
FIG. 19 shows the use of the lock ring from FIG. 12 to secure each rod as part of another embodiment.

Another embodiment is shown in FIG. 19 wherein a pair of lock rings 208b are used at each end of device 50 once device 50 has been fully deployed. Different sized lock rings 208b can be provided to accommodate the different diameters of each rod 54. When lock rings 208b are used as shown in FIG. 19, lateral movement of device 50 is restricted. Different configurations of lock rings 208b may also be provided. For example, the side of lock ring 208b that abuts a vertebral body may be flared to provide greater mechanical contact between the lock ring 208b and the adjacent vertebral body.

Figure 20:
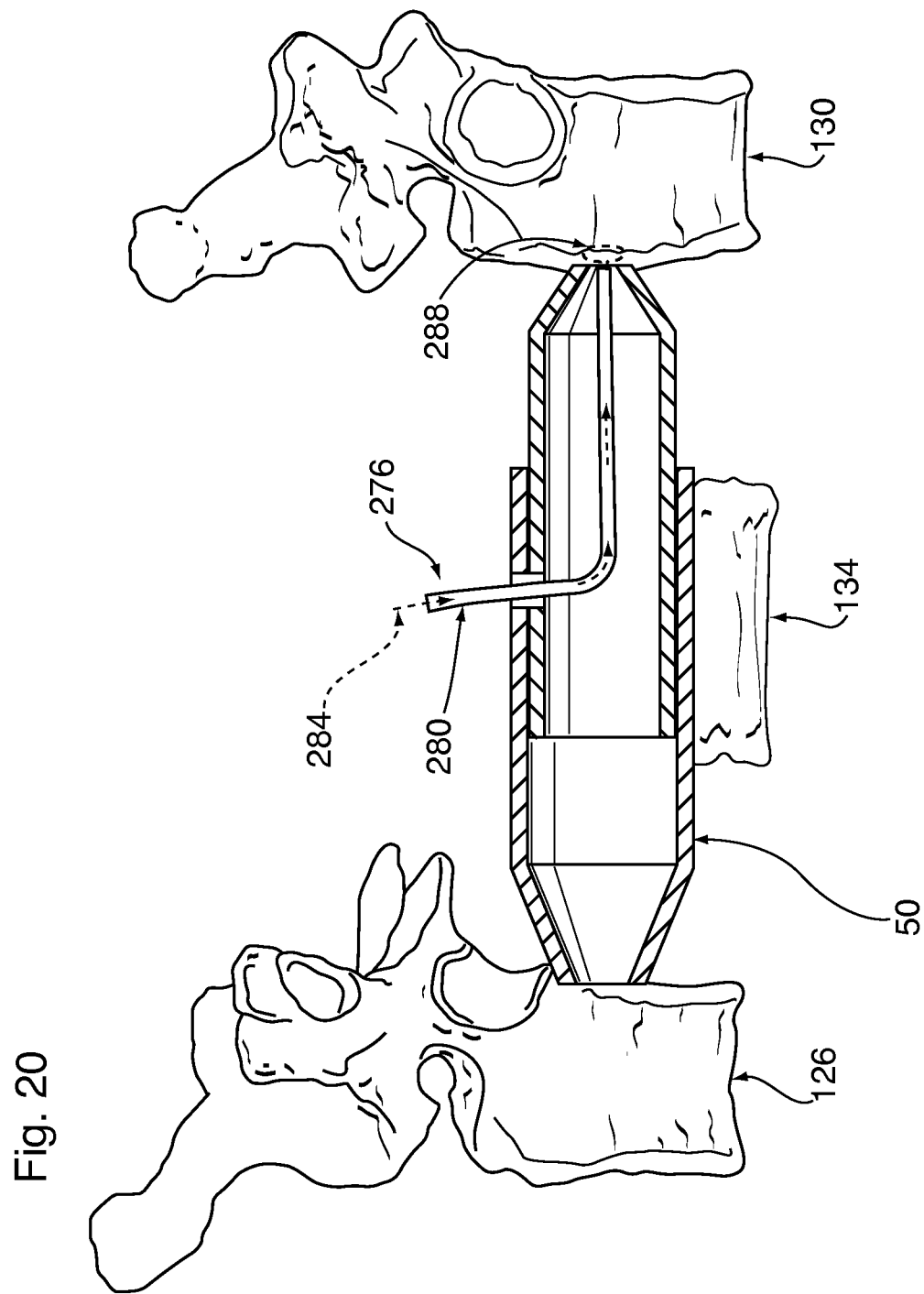
FIG. 20 shows a hollowing instrument as another embodiment.

Another embodiment is shown in FIG. 20 which shows a hollowing instrument 276 that comprises a flexible sleeve 280 and a semi-rigid articulating arm 284 that passes through sleeve 280. Sleeve 280 and arm 284 are passed through device 50, as shown, and into vertebral body 130. The tip 288 of articulating arm 284 comprises a cutting surface to hollow out a small portion of vertebral body 130 to accommodate the tip of device 50 and bone cement. The hollowing instrument 276 can create cavity to receive either kyphoplasty balloon or bone cement. It will thus be now be apparent that the teachings herein can be used to optionally deploy a kyphoplasty balloon.

Figure 21:
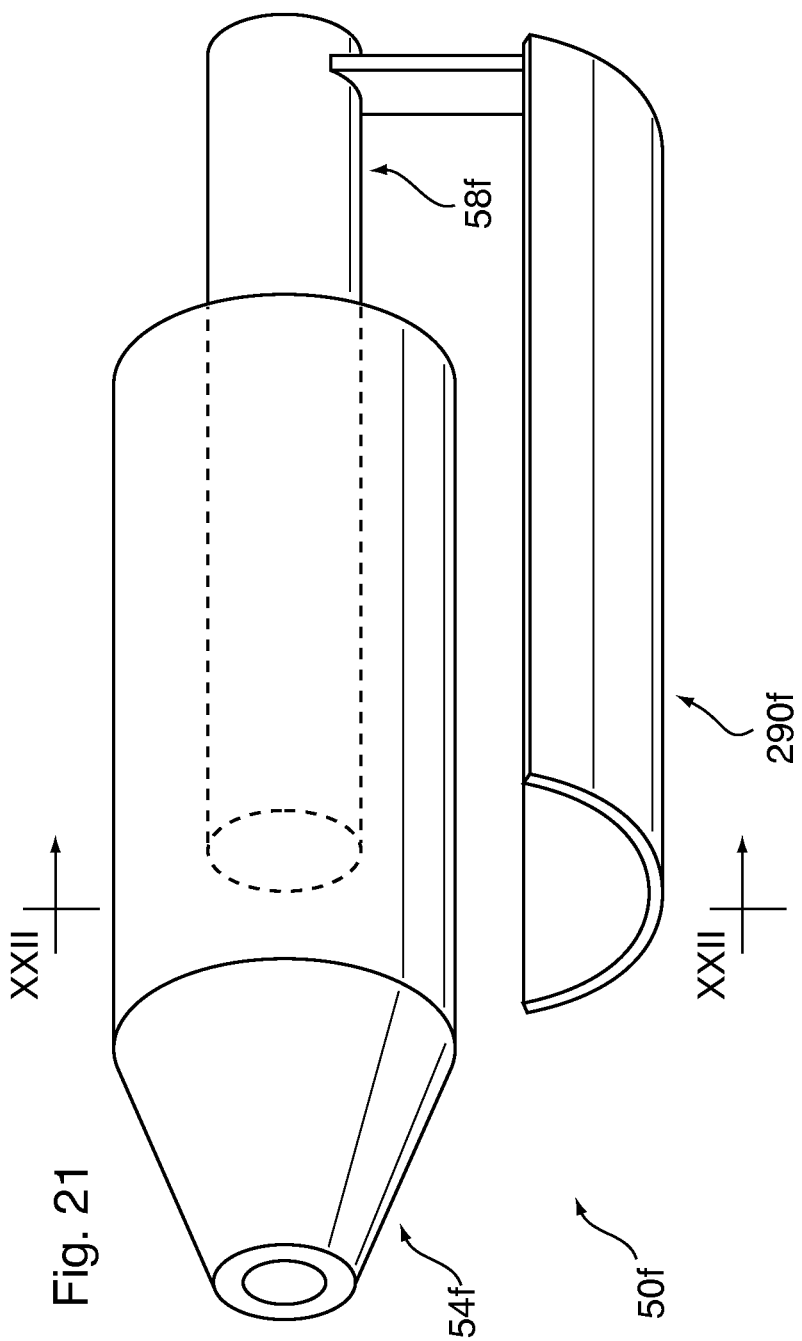
FIG. 21 shows an alternative embodiment with a drip tray.

A further embodiment is shown in FIG. 21, in a further variation of device 50f where a drip tray 290f is provided along rod 58f. Drip tray 290f can be provided to capture excess PMMA and which can they flow along the length of drip tray 290f.

While various embodiments have discussed the use of rings or clamps or crimps to secure rod 54 and rod 58 it is contemplated that additional mechanical strength is provided by the cured PMMA.

It will now be apparent that the present specification contemplates many variations. The choice of a particular variation can be based on surgical considerations as to the best possible outcome for a particular patient. For example, in a high thoracic (neck area) procedure, it may be desired to select solid versions of device 50, but in a mid lumbar region, a canulated version of device 50 may be more desired.

The invention claimed is:

1. A spinal implant device for implanting at a site of a target vertebral body between a first adjacent vertebral body and a second adjacent vertebral body comprising:
   a first rod;
   a first tip connected to said first rod, said first tip having a proximal end having a width substantially the same as a width of said first rod where said first tip proximal end connects to said first rod, said first tip having a distal end having a width narrower than the first tip proximal end width, the first tip distal end being configured for piercing into the first adjacent vertebral body;
   a first port in the first rod and configured to pass a bone cement to a channel of the first rod;
   a second rod coaxially slidable within and in relation to said first rod;
   a second tip connected to said second rod, said second tip having a proximal end having a width substantially the same as a width of said second rod where said second tip proximal end connects to said second rod, said second tip having a distal end having a width narrower than the second tip proximal end width, the second tip distal end being configured for piercing into the second adjacent vertebral body;
   a second port in the second rod and configured to pass the bone cement to a channel of the second rod, when the first and second ports are in registration; and
   the first and second rod channels each being configured for flowing the bone cement through at least one of said tips.

2. The device of claim 1 wherein the bone cement comprises polymethylmethacrylate.

3. The device of claim 1 wherein at least one of said rods is hollow.

4. The device of claim 1 further comprising a mechanical fastener configured for securing said first rod and said second rod with respect to each other.

5. The device of claim 4, wherein said mechanical fastener comprises a crimp having one or more dimples applied along a portion of at least one of said rods.

6. The device of claim 4, wherein the mechanical fastener comprises a set screw.

7. The device of claim 4, wherein the mechanical fastener comprises a lock ring.

8. The device of claim 4, wherein the mechanical fastener comprises plural lock rings.

9. The device of claim 1 wherein an outer surface of at least one of said rods comprises at least one boss.

10. The implant of claim 1 wherein each of said first rod and said second rod includes a cylindrical section, each said cylindrical section having a solid surface.

11. A spinal implant for implantation between a first adjacent vertebral body and a second adjacent vertebral body, comprising:
   a first rigid rod;
   a first tip connected to said first rigid rod, a width of said first tip being the same as a width of said first rigid rod where said first tip connects to said first rod, said first tip configured for piercing into the first adjacent vertebral body;
   a second rigid rod coaxially slidable within and in relation to said first rigid rod;
   a second tip connected to said second rigid rod, a width of said second tip being the same as a width of said second rigid rod where said second tip connects to said second rigid rod, said second tip configured for piercing into the second adjacent vertebral body;
   at least one of said rods comprising a channel in communication with said tip of said at least one of said rods; and
   a bone cement disposed between (i) said first tip where it pierces into said first adjacent vertebral body and (ii) said tip where it pierces into said second adjacent vertebral body, the bone cement surrounding at least a portion of said first rigid rod and said second rigid rod, said rods providing reinforcement to said bone cement between said first tip and said second tip;
   wherein said first rod and second rod have a diameter smaller than a length of said spinal implant.

12. The implant of claim 11 wherein an outer surface of at least one of said rods comprises at least one boss.

13. The implant of claim 11 wherein said first rod and said second rod include a cylindrical section, each said cylindrical section having a solid surface.

14. The implant of claim 13 wherein said at least one rod comprising said channel includes a port providing communication from the exterior of said at least one rod to said channel.

15. The implant of claim 14, wherein both said rods comprise a channel and a port, and wherein overlapping said two ports provides communication from the exterior of said first rod to said channel comprised within said second rod.

* * * * *